(12) United States Patent
Mönkemöller

(10) Patent No.: US 7,461,540 B2
(45) Date of Patent: Dec. 9, 2008

(54) METAL-OXIDE GAS SENSOR

(76) Inventor: Ralf Mönkemöller, Wiedehopfweg 20, Gütersloh (DE)

(*) Notice: Subject to any disclaimer, the term of this patent is extended or adjusted under 35 U.S.C. 154(b) by 0 days.

(21) Appl. No.: 11/799,080

(22) Filed: Apr. 30, 2007

(65) Prior Publication Data
US 2007/0254812 A1  Nov. 1, 2007

(30) Foreign Application Priority Data
Apr. 29, 2006  (DE) ........................ 10 2006 020 113

(51) Int. Cl.
*G01N 27/02* (2006.01)
(52) U.S. Cl. ............... 73/25.05; 73/25.01; 73/31.05; 73/31.06
(58) Field of Classification Search ........... 73/25.01, 73/25.05, 31.05, 31.06
See application file for complete search history.

(56) References Cited

U.S. PATENT DOCUMENTS 5,012,671 A * 5/1991 Yagawara et al. .......... 73/31.06
5,777,207 A * 7/1998 Yun et al. .................. 73/31.05

FOREIGN PATENT DOCUMENTS

| JP | 61-275648 A | * | 12/1986 | .......... 73/31.05 |
| JP | 1-301158 A | * | 12/1989 | .......... 73/31.05 |
| JP | 4-128645 A | * | 4/1992 | .......... 73/25.01 |
| JP | 5-52791 A | * | 3/1993 | .......... 73/31.05 |
| JP | 6-11472 A | * | 1/1994 | .......... 73/31.05 |
| WO | WO 2004/048956 | * | 6/2004 | |
| WO | WO 2004/051261 | * | 6/2004 | |

* cited by examiner

*Primary Examiner*—Daniel S Larkin

(57) ABSTRACT

A gas sensor has a dielectric base having a face, a heater element on the face, electrodes connected to the heater element, and a gas sensor element on the heater element that when heated changes impedance when in contact with a predetermined gas. The element is in electrical contact with the heater element. A power supply connected to the heater element electrodes energizes same and heats the gas sensor to its operating temperature. A sensor electrode is also in contact with the sensor element so that the impedance of the sensor element can be measured between the sensor electrode and one of the heater element electrodes.

7 Claims, 2 Drawing Sheets

METAL-OXIDE GAS SENSOR

FIELD OF THE INVENTION

The present invention relates to a gas sensor. More particularly this invention concerns a solid-state, normally metal-oxide, gas sensor.

BACKGROUND OF THE INVENTION

A metal-oxide gas sensor has a dielectric base carrying two electrodes that are typically embodied as an interdigital structure (IDT) and a gas-sensitive element whose electrical conductivity varies according to the concentration of a measured gas component. Two electrodes form the interdigital structure and are connected to the gas-sensitive element. The base also carries a resistive heater element having energizing electrodes. All the electrodes terminate at one edge of the base, which typically is formed as a basically rectangular plastic plate.

Such a sensor is described for instance in DE 196 06 272 of O. Kiesewetter. Its heater element surrounds the interdigital structure, the actual sensor element being formed by means of the interdigital structure and the sensor element in contact with it. Compared to such sensors where the heater element and the interdigital structures are mounted on different faces of the base or insulator, production engineering advantages result due to the provision of the interdigital structure, the sensor element, and the heater element on the same face of the base or insulator. However, heat distribution is not uniform because the resistive heater element surrounds the interdigital structures. Very frequently this causes sensor behavior that is too non-specific, rendering it difficult or sometimes impossible to reliably control corresponding concentrations of measured gas values. Another disadvantage of this arrangement is that, given a required minimum surface area of the sensor element, the space needed on the base is greater than this minimum surface area and requires that the sensor unit be relatively large.

OBJECTS OF THE INVENTION

It is therefore an object of the present invention to provide an improved metal-oxide gas sensor.

Another object is the provision of such an improved metal-oxide gas sensor that overcomes the above-given disadvantages, in particular that is very compact and that provides very accurate and reliable readings.

Yet another object is to provide such a sensor unit that is very inexpensive to manufacture.

SUMMARY OF THE INVENTION

A gas sensor has according to the invention a dielectric base having a face, a heater element on the face, electrodes connected to the heater element, and a gas sensor element on the heater element that when heated changes impedance when in contact with a predetermined gas. The element is in electrical contact with the heater element. A power supply connected to the heater element electrodes supplies electricity to the heater element and heats the gas sensor to its operating temperature. A sensor electrode is also in contact with the sensor element so that the impedance of the sensor element can be measured between the sensor electrode and one of the heater element electrodes.

An interdigital structure is used for contacting the sensor element if the heater element is a meander and if the second electrode has fingers that are joined to one another and fitted between the more or less parallel sections of the meander heater element.

The second required electrode can be almost any suitable configuration. Very good homogenous features are attained when the second electrode is formed by a conductor that runs at a fixed distance parallel to the path of the heater element, which typically is formed as a resistive trace on the respective face of the base.

An inventive sensor configured in this manner can provide very uniform heat distribution for the sensor element of the actual sensor element, with significant production engineering savings, by integrating the heater element into the actual sensor element.

This is particularly true when each of the fingers of the second electrode that are joined to one another extends across the entire length of two sections of the meander, with more or less parallel sections of the meander heater element therebetween.

Electric current is applied to the heating element until the operating temperature of the sensor element is attained. Once the operating temperature has been attained, the heating current applied to the heating structure is preferably turned off. The conductance of the sensor element is measured via the heater element and the second electrode. Then the heating current applied to the heater element can be turned on again.

Advantageously, a plurality of sensors can be embodied on one base if a plurality of separate electrodes with meander heater elements each form an interdigital structure.

If at least one additional interdigital structure and a respective sensor element are mounted on the other face of the base or insulator, the sensor can detect two different gases. If the sensor element that is mounted on the other face of the base or insulator has a lower operating temperature than the sensor element on the one face of the base or insulator, the heat energy of the heater element mounted on the one face of the base or insulator can be adequate for operating the sensor element on the other face of the base or insulator.

If the sensor elements on the different faces of the base or insulator work at approximately the same operating temperature, it is advantageous when a heating element is also provided on the other face of the dielectric base.

In accordance with another advantageous embodiment of the inventive sensor, the interdigital structure mounted on the other face of the base or insulator, where necessary the heater element and the sensor element are set up like the interdigital structure, the heater, and the sensor on the other face of the base or insulator.

Of course it is also possible to configure or arrange a plurality of the sensors described in the foregoing on both faces of the base or insulator, the meander heater element advantageously being a common component for a plurality or all of the sensors embodied in this manner.

The second electrode formed from the conductors joined to one another can be replaced by any desired suitable conductor geometry that can be adapted to the requirements for the specific circumstances.

The second electrode, as well, can be an additional heater element structure, the resistance of the sensor element being measurable then between the two heater elements.

Moreover, the heater element can be common electrodes of a plurality of individual sensor arrangements.

In accordance with another advantageous embodiment of the inventive sensor, applied to the face of the base that faces away from the heater element are one or a plurality of interdigital structures by means of which the resistance of different sensor elements can be measured, heating of the sensor elements being effective through the insulator by means of the heater element.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
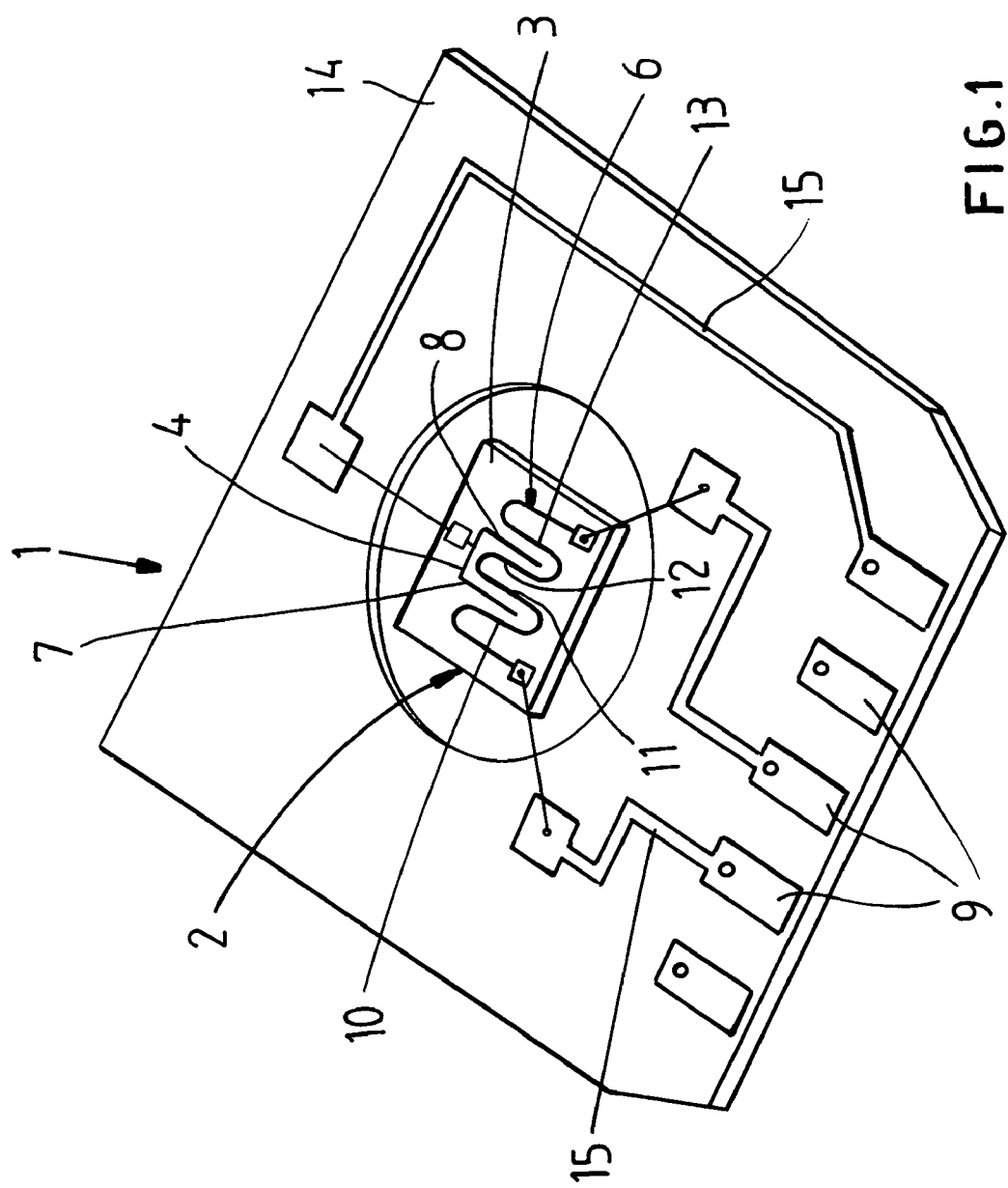
FIG. 1 is a-perspective view of the top face of a gas-sensor unit according to the invention with the actual gas sensor element not shown for clarity of view.
Figure 2:
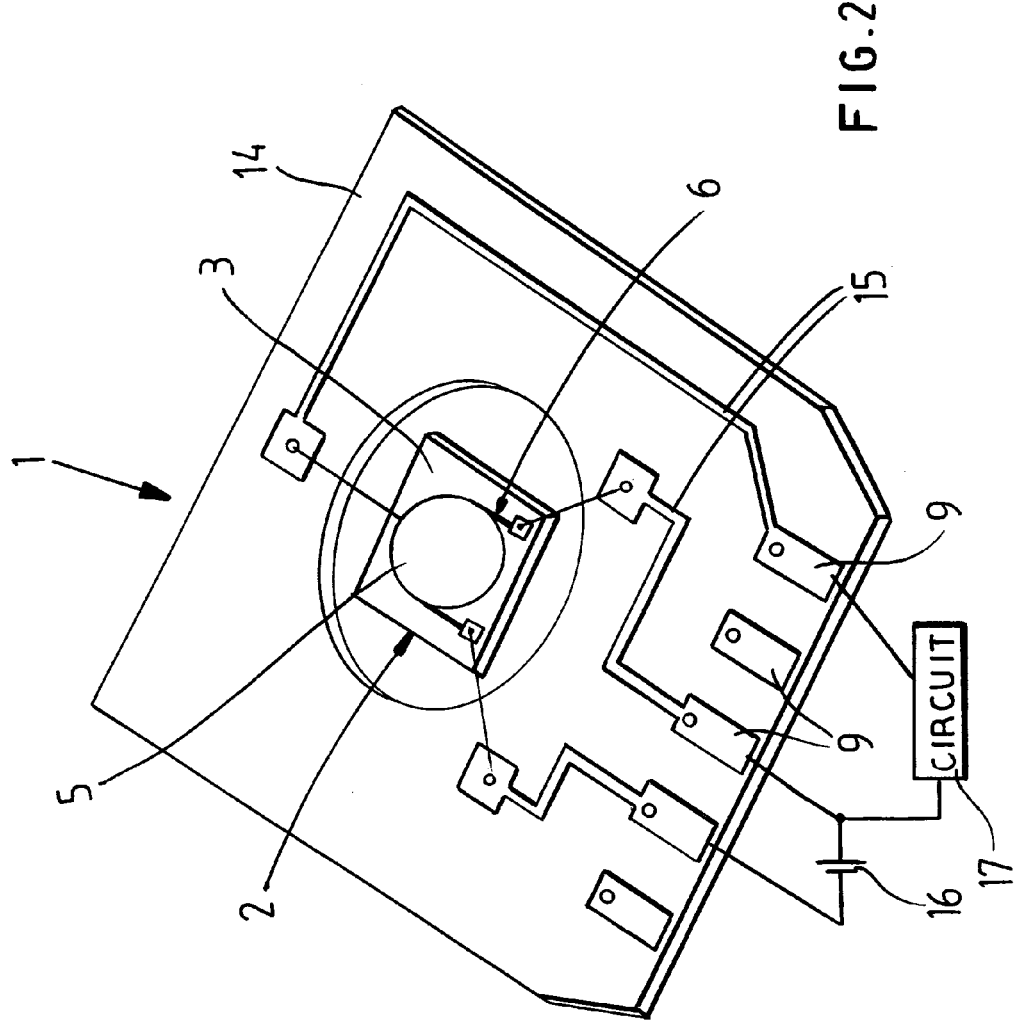
FIG. 2 is a view like FIG. 1 of the bottom face of the unit, but with the sensor element in place.

As seen in FIG. 1 a gas-sensor unit 1 has a sensor subassembly 2 carried on a basically rectangular dielectric, e.g. ceramic or silicon, base plate 3 itself mounted on a standard plastic card 14 having traces 15 and a plurality of edge contacts 9. The structure on both faces of the plate 3 is identical, so in the following, for simplicity's sake, only the structure on one face is described. One sensor conductor 4 formed as a trace on the base 3 is connected via a respective trace 15 to a respective contact 9 and has a pair of parallel arms or fingers 7 and 8 that underlie a sensor metal-oxide element or foil 5 (FIG. 2 only). A meander heater element 6 also formed as a trace on the base 3 has ends connected to respective traces 15 connected in turn to respective contacts 9. Both the heater element 6 and the conductors 4, 7, and 8 are on the same face of the base plate 3.

As can be seen in particular from FIG. 1, the conductors 4, 7, 8 that are joined to one another include the fingers 7 and 8 that are parallel to one another and that are joined to the conductor 4, so that the fingers 7 and 8 form a U with the conductor 4 as the bight of the U. Here there are two fingers 7 and 8 that are interdigitated with sections 10, 11, 12, and 13 of the meander heater element 6 that are parallel to one another. Any other desired number is conceivable in this case. The fingers 7 and 8 extend across approximately the entire length of the sections 10, 11 and 12, 13 of the meander heater element 6 that are parallel to one another.

This means that the fingers 7 and 8 of the conductors 4, 7 and 8 that are joined to one another and the heater element 6 embodied by the meander heater element 6 are interdigitated or interleaved with one another to form an interdigital structure. Thus the resistance of the sensor element 5 shown placed thereover in FIG. 2 is measurable as an impedance between the conductors 4, 7, and 8 on one side and the heater element 6 on the other. This resistance of the sensor element 5 is thus measured at a plurality of measuring points for a very accurate output.

For operating the sensor 2, the latter is heated by electrically energizing the meander heater element 6, with electrical current to its operating temperature, which is approx. is 300 degrees C. if the sensor 2 is a metal-oxide gas sensor. The electrical current is turned off once the operating temperature of the sensor 2 is attained. The resistance is measured via the heater element 6 and the conductors 4, 7 and 8 that are joined to one another. Then the electrical current is turned on again for operating the meander heater element 6.

In this system a power supply or battery illustrated schematically at 16 is connected to the two terminals 9 connected to the ends of the heater element meander 6 to electrically energize it and heat the sensor element 5. In addition a circuit 17 is connected to one of the terminals 9 of one of the heater element ends and to the terminal connected to the conductors 4, 7, and 8 to measure the impedance between the heater element 6 and the conductors 4, 7, and 8 and thereby determine the concentration of whatever gas the sensor element 5 responds to. In fact the common terminal shared by the circuit 17 and power supply 16 can be the ground connection of the device 1, which is here shown with five terminals that can serve other purposes or as described below for another sensor unit 2 on the other face of the base 3.

Due to the arrangement of the conductors 4, 7 and 8 of the sensor element 5 that are joined to one another and the heater element 6 on the same face of the base or insulator 3, at least one additional sensor element can be mounted on the other face of the base or insulator 3 to create a more complex sensor. If a sensor element mounted on the other face of the base or insulator 3 has a lower operating temperature than that of the sensor element 5 on the one face of the base or insulator 3, the heater element 6 provided on the one face can be adequate for the entire sensor 2, and in this case a second sensor electrode is provided. If the sensor elements 5 provided on the different faces of the base 3 have more or less the same operating temperature, a heater element must be provided for each sensor element.

The system of FIG. 2 can differ from that of FIG. 1 not only by not having its own heater element 6, but by having two such heater elements that are interdigitated with each other. In this case the circuit 17 for this unit is connected between the two heaters.

I claim:

1. A gas sensor comprising:
   a dielectric base having a face;
   a heater element on the face;
   electrodes connected to the heater element;
   a gas sensor element on the heater element that when heated changes impedance when in contact with a predetermined gas, the element being in electrical contact with the heater element;
   means connected to the heater element electrodes for energizing the electrodes and heating the gas sensor; and
   a sensor electrode also in contact with the sensor element, whereby the impedance of the sensor element can be measured between the sensor electrode and one of the heater element electrodes.

2. The gas sensor defined in claim 1, further comprising circuit means connected to the sensor electrode and the one heater element electrode for measuring the impedance of the sensor element.

3. The gas sensor defined in claim 1 wherein the heater element is a resistive heater trace on the one face and the sensor electrode is another trace having a portion adjacent the heater trace.

4. The gas sensor defined in claim 3 wherein the heater trace is a meander with a plurality of parallel sections, the sensor electrode having fingers interleaved with the sections of the heater trace.

5. The gas sensor defined in claim 1 wherein the base has two such faces each provided with a respective such sensor element and sensor electrode.

6. The gas sensor defined in claim 5 wherein each face is provided with a respective such heater element.

7. The gas sensor defined in claim 1 wherein the sensor electrode is also constituted as a heater element.

* * * * *